United States Patent [19]

Schwen et al.

[11] Patent Number: 5,344,651
[45] Date of Patent: Sep. 6, 1994

[54] CYPROTERONE ACETATE THIOACETATE

[75] Inventors: Richard J. Schwen, Cincinnati; Mark R. Sine, Morrow; Raphael Warren, Amberly Village, all of Ohio

[73] Assignee: The Procter & Gamble Company, Cincinnati, Ohio

[21] Appl. No.: 96,086

[22] Filed: Jul. 23, 1993

[51] Int. Cl.$^5$ .............................................. A61K 7/00
[52] U.S. Cl. .................................... 424/402; 424/401; 424/70; 514/178; 552/585
[58] Field of Search .................... 514/178; 552/585; 424/401, 402

[56] References Cited

U.S. PATENT DOCUMENTS

| | | | |
|---|---|---|---|
| 4,177,268 | 12/1979 | Torossian et al. | 424/243 |
| 4,269,778 | 5/1981 | Torossian et al. | 260/397.45 |
| 4,361,559 | 11/1982 | Varma | 424/243 |
| 4,861,765 | 8/1989 | Mitsukuchi et al. | 514/181 |
| 4,877,781 | 10/1989 | LeHaye et al. | 514/179 |
| 5,021,408 | 6/1991 | Aubard et al. | 514/179 |

FOREIGN PATENT DOCUMENTS

86/01402  3/1986  World Int. Prop. O. .

OTHER PUBLICATIONS

Bettendorf, G., "Effect of Cyproterone in Female Virilizing Syndromes", Proceedings of 3rd Meeting of International Study Group on Steroid Hormones, vol. 3, 267–276 (1968).
Bodor, N. "The Application of Soft Drug Approaches to the Design of Safer Corticosteroids", Topical Cortoscosteroid Therapy: A Novel Approach to Safer Drugs, pp. 13–25 (1988).
Bodor, N. "Soft Drugs: Prinicples and Methods for the Design of Safe Drugs", Medicinal Research Reviews, vol. 4, No. 4, pp. 449–469 (1984).
Bodor, N. and K. B. Sloan, "Soft Drugs V: Thiazolidine-Type Derivatives of Progesterone and Testosterone", Journal of Pharmaceutical Sciences, vol. 71, No. 5, pp. 514–520 (May 1982).
Burton, J. L., U. Laschet and S. Shuster, "Reduction of Sebum Excretion in Man by the Antiandrogen, Cyproterone Acetate", British Journal of Dermatology, vol. 89, pp. 487–490 (1973).
Chanoine, F. and J. L. Junien, "Comparative Pharmacokinetic Studies of Tixocortol Pivalate and Cortisol in the Rat", J. Steroid Biochem, vol. 21, No. 4, pp. 453–459 (1984).
Cunliffe, W. J. S. Shuster and A. J. Cassels Smith, "The Effect of Topical Cyproterone Acetate on Sebum Secretion in Patients With Acne,", Br. J. Derm., vol. 81, No. 3, pp. 200–201 (1969).
Dawber, R. P. R., T. Sonnex and I. Ralfs, "Oral Anti--androgen Treatment of Common Baldness in Women", B. J. Derm., Suppl. 22, vol. 107, p. 20 (1982).
Devlin, R. G., A. Dean, K. Kripalani, J. R. Taylor and A. A. Sugerman, "Percutaneous Absorption and Adrenal Suppressive Potency of Tipredane, A New Topical Corticosteroid", J. Toxicol ... —Cut. & Ocular Toxicol., vol. 5, No. 1, pp. 35–43 (1986).
Huber, J., R. Zeillinger, J. Spona, J. Schmidt, U. Täuber and W. Kuhnz, "Parenteral and Peroral Cyproterone Acetate (CPA) in Severe Hirsutism", Proceedings of World Congress of Dermatology, Berlin, May 24–29, 1987.
Lan, S. J., L. M. Scanian, S. H. Weinstein, R. K. Varma, B. M. Warrack, S. E. Unger, M. A. Porubcan and B. H.

(List continued on next page.)

Primary Examiner—Thurman K. Page
Assistant Examiner—Neil Levy
Attorney, Agent, or Firm—D. L. Suter; M. B. Graff, IV; S. G. Simon

[57] ABSTRACT

The present invention relates to the compound cyproterone acetate thioacetate (CATA) and compositions comprising CATA. The present invention further relates to methods of treating acne and/or sebaceous gland activity comprising topical application of CATA. The present invention additionally relates to methods of regulating hair growth comprising application of compositions comprising CATA.

11 Claims, No Drawings

OTHER PUBLICATIONS

Migdolf, "Biotransformation of Tipredane, A Novel Topical Steroid, In Mouse, Rat, and Human Liver Homogenates", Drug Metabolism and Disposition, vol. 17, No. 5, pp. 532–541.

Lan, S. J., L. M. Scanian, J. Mitroka, S. H. Weinstein, B. N. Lutsky, C. A. Free, R. J. Wonjar, R. C. Millonig and B. H. Migdalof, "Rapid Metabolic Inactivation of Tipredane, A. Structurally Novel Topical Steroid", Journal of Steroid Biochemistry, vol. 31, No. 5, pp. 825–834 (1988).

Larochelle, P. P. Du Souich, E. Bolte, J. Lelorier and R. Goyr, "Tixocortol Pivalate, a Corticosteroid With No Systemic Glucocorticold Effect After Oral, Intrarectal, and Intranasal Application", Clin. Pharmacol. Ther., vol. 33, No. 3, pp. 343–350 (Mar. 1983).

Lutsky, B. N., R. C. Millonig, R. J. Wojnar, C. A. Free, R. G. Devlin, R. K. Varma and D. S. Karanewsky, "Androstene-17-thioketals", Arzneim.-Forsch./Drug Res. vol. 36(II), No. 12, pp. 1787–1795 (1986).

Lyons, F. and S. Shuster, "Indirect Evidence That The Action of Cyproterone Acetate On The Skin is Due To A Metabolite", Clinical Endocrinology, vol. 19, pp. 53–55 (1983).

Matias, J. and N. Orentreich, "The Effect of Androgens, Antiandrogens and Vasodilating Agents on Hair Loss in the Androchronogenetic Alopecia (AGA)—Mouse Model", Proceedings of World Congress of Dermatology, Berlin, May 245–29, 1987.

Neumann, F., R. von Berswordt-Wallrabe, W. Elger, H. Steinbeck, J. D. Hahn and M. Kramer, "Aspects of Androgen-Dependent Events as Studied by Antiandrogens", Recent Progress in Hormone Research, vol. 26, pp. 337–410 (1970).

Pye, R. J., J. L. Burton and J. I. Harris, "Effect of 1% Cyproterone Acetate in Cetamocrogol Cream BPC (Formula A) on Sebum Excretion Rate in Patients With Acne", British Journal Of Dermatology, vol. 95, No. 4, pp. 427–428 (Oct. 1976).

Vermorken, A. J. M., "Reversal of Androgenic Alopecia by Minoxidil: Lack of Effect of Simultaneously Administered Intermediate Doses of Cyproterone Acetate", ACTA Dermatovener, vol. 63, pp. 268–269.

Vogit, W. and S. L. Hsia, "Further Studies on Testosterone $5_\alpha$–Reductase of Human Skin", The Journal of Biological Chemistry, vol. 218, No. 12, pp. 4280–4285 (Jun. 1973).

Wendt, H., S., H. Hasan, I. Heinze and U. Tauber, "Systemic Effects of Local Antiandrogen Therapy", Arch. Dermatol. Res., vol. 273, p. 171 (1982).

Wiechert, Neumann, "Cyproterone", The Merck Index, 11th Edition, p. 435.

Wojnar, R. J., R. K. Varma, C. A. Free, R. C. Millonig, D. Karanewsky and B. N. Lutsky, "Androstene-17-thioketals,", Arzneim.-Forsch./Drug. Res., vol. 36(II), No. 12, pp. 1782–1787 (1986).

CYPROTERONE ACETATE THIOACETATE

TECHNICAL FIELD

The present invention relates to the field of sebum control and treatment of acne in mammalian skin and scalp. The present invention also relates to the field of regulating hair growth.

BACKGROUND

Acne

The pilosebaceous gland is a principal source of oil on mammalian skin and scalp. Therefore, a benefit of controlling sebaceous gland activity (sebum secretion) includes a reduction in the level of oil found in skin and hair.

Sebum secretion is also related to acne. Acne is a pilosebaceous disease characterized by comedo, papules, inflamed nodules and superficial pus-filled cysts. The course and severity of acne is determined by the interaction between hormones, keratinization, sebum formation and bacteria. Acne usually begins at puberty, when circulating levels of androgens increase. The pilosebaceous glands increase in size and sebum synthetic activity is elevated due to this increase in circulating levels of androgens. Follicular hyperkeratosis can also occur, causing restriction of pilosebaceous follicles and, consequently, comedo or plug formation. The comedo contains sebum, protein debris, and anaerobic microorganisms including propionibacterium (cotynebacterium) acnes (P. acnes). P. acnes thrives on the sebum and generates inflammatory free fatty acids (FFA). The FFA cause irritation in the follicular wall and can lead to rupture of the follicular wall, inducing an inflamed lesion. In severe cases, this lesion will heal with scarring.

Existing treatments for acne include from general topical application of lotions and salves to affected skin areas, to localized (spot) topical treatment. Products used for such treatments include benzoyl peroxide, sulfur resorcinol, salicylic acid and trans-retinoic acid. The therapeutic value is limited because of poor efficacy, poor aesthetics, and lack of effect on sebum production.

Other effective therapies for acne which reduce sebum production, include the use of antiandrogens, and cis-retinoic acid. However, because of undesirable systemic side effects, such as teratogenecity, pituitary dysfunction, and male sterility, current use is restricted to the more severe cases of acne. Antimicrobials are also somewhat effective in treating acne because they control the growth of P. acnes. The effectiveness of antimicrobials is limited because they do not affect sebum production.

For the foregoing reasons, there is a need for an efficacious, easily administered, agent for treating acne and/or reducing sebaceous gland activity in a mammal, having little or no undesirable side effects.

Hair Growth

Society in general continues to attach a stigma to hair loss. Men and women suffer from hair loss, often resulting in self-consciousness relating to the hair loss. Domestic animals, such as cats and dogs, also suffer from hair loss. While the animal is not likely to be emotionally affected by such hair loss, its owner may be, particularly if such an animal is to be shown in various competitions. Additionally, increased hair growth in livestock such as sheep, thereby resulting in increased wool production, is also desirable. The desire for a healthy full head (or body, in the case of animals) of hair has resulted in a variety of approaches to the "curing" of hair loss.

One such approach involves the much publicized use of minoxidil (6-(1-piperidinyl)-2,4-pyrimidinediamine 3-oxide), a potent antihypertensive agent, as a hair growth promoting agent (see U.S. Pat. Nos., 3,461,461; 3,973,061; 3,464,987; and 4,139,619). Unfortunately, not all people respond to minoxidil and the efficacy level is limited in those individuals exhibiting a response.

Another approach for "curing" hair loss involves a procedure of weaving synthetic or natural hair strands into the remaining hair strands of the subject. Such a procedure is time consuming, expensive and requires follow-up re-weavings as the weaves loosen and/or the subject's existing hair strands grow. Furthermore, such a procedure does not cure hair loss, but merely masks the condition.

Another approach for treating hair loss is the use of hair plugs. This procedure involves the transplantation of terminal hair follicles from regions of normal hair growth on the subject's scalp to regions of thinning or no hair growth on the scalp. The procedure is time consuming, expensive and can be painful. Furthermore, the transplanted plugs, at least in the early stages following transplantation, produce an unnatural look to the scalp.

For the foregoing reasons, there is a need for an easily administered, efficacious agent for treating hair loss in a mammal having little or no undesirable side effects.

OBJECTS OF THE PRESENT INVENTION

It is an object of the present invention to provide compounds useful for treating acne and/or sebaceous gland activity and/or regulating hair growth.

It is also an object of the present invention to provide compositions useful for treating acne and/or sebaceous gland activity and/or regulating hair growth.

It is also an object of the present invention to provide methods for treating acne and/or sebaceous gland activity.

It is also an object of the present invention to provide methods for regulating hair growth.

SUMMARY

The present invention is directed to cyproterone acetate thioacetate (hereinafter "CATA") and compositions comprising CATA. Such a compound and compositions satisfy the need for an efficacious, easily administered agent for treating acne and/or sebaceous gland activity, having little or no undesirable side effects. Such a compound and compositions also satisfy the need for an efficacious, easily administered agent for regulating hair growth, having little or no undesirable side effects. The present invention is further directed to a method of treating acne and/or sebaceous gland activity in the skin of a mammal susceptible to or having acne, comprising application of a composition of the present invention. The present invention is further directed to a method of regulating hair growth in a mammal (e.g., humans and domestic animals) susceptible to or suffering from hair loss, comprising application of a composition of the present invention.

The compositions of the present invention relating to the acne treatment or hair growth regulation embodiments comprise a safe and effective amount of CATA and a pharmaceutically-acceptable or cosmetically-acceptable carrier.

These and other features, aspects and advantages of the present invention will become better understood with reference to the following description and appended claims.

DETAILED DESCRIPTION

As used herein, "cyproterone acetate thioacetate" and "CATA" mean a compound having the structure:

As used herein, "topical application" means directly laying on or spreading on outer skin.

As used herein, "cutaneous injection" means introduction of a substance beneath or within the skin by a hypodermic needle; preferably proximate to the site of desired response.

As used herein, "safe and effective amount" means a sufficient amount of a composition to provide a desired hair growth regulating or acne and/or sebaceous gland activity treating effect (whichever the case may be).

As used herein, "comprising" means that other steps and other ingredients which do not affect the end result can be added. This term encompasses the terms "consisting of" and "consisting essentially of".

As used herein, "pharmaceutically-acceptable" means that drugs, medicaments or inert ingredients which the term describes are suitable for use in contact with the tissues of humans and lower animals without undue toxicity, incompatibility, instability, irritation, allergic response, and the like.

As used herein, "cosmetically-acceptable" means that ingredients which the term describes are suitable for use in contact with the skin of humans and lower animals without undue toxicity, incompatibility, instability, irritation, allergic response, and the like.

Acne

As used herein "treating sebaceous gland activity" means preventing, retarding and/or arresting the production of sebum.

As used herein "treating acne" means preventing, retarding and/or arresting the process of acne formation.

It has been unexpectedly discovered that CATA, when administered to a mammal, in a safe and effective amount, can treat ache and/or sebaceous gland activity.

Compositions useful for treating acne and/or sebaceous gland activity preferably comprise from about 0.0001% to about 10% of CATA, more preferably from about 0.001% to about 5%, more preferably still from about 0.01% to about 2%, more preferably still from about 0.1% to about 1%.

Hair Growth

As used herein, "regulating hair growth" means increasing the rate of hair growth and/or inducing the formation of a greater number of hair strands, and/or increasing the diameter of the hair strand, and/or lengthening the hair strand, and/or changing the hair follicle from vellus to terminal, and/or converting follicles from telogen to anagen phase (thereby increasing the overall ratio of anagen phase follicles relative to telogen phase follicles) and/or preventing, retarding, or arresting the process of hair loss, and/or treating alopecias.

As used herein, "vellus hair follicle" means a hair follicle which produces a soft, short, and often colorless hair fiber. The size of the vellus follicle is considerably smaller than the terminal hair follicle. In an adult, vellus follicles can be found on the forehead (i.e., receding hair line area) and bald scalp.

As used herein, "terminal follicle" means a hair follicle which produces a coarse, long, and often pigmented hair follicle. The size of the terminal follicle is considerably larger, thicker in diameter and longer than the vellus follicle. In the adult, terminal follicles can be found on the scalp, axilla and pubic areas.

As used herein, "anagen phase" refers to the period in the hair follicle growth cycle wherein the follicle is actively growing and producing new hair.

As used herein, "telogen phase" refers to the period in the hair follicle growth cycle wherein the follicle is resting and not producing new hair.

It has been unexpectedly discovered that CATA, when administered to a mammal (e.g., human or domestic animal), in a safe and effective amount, can regulate hair growth.

Compositions useful for regulating hair growth preferably comprise from about 0.0001% to about 10% of CATA, more preferably from about 0.001% to about 5%, more preferably still from about 0.01% to about 2%, more preferably still from about 0.1% to about 1%.

The Carrier

The compositions of the present invention comprise a solid, semi-solid or liquid cosmetically and/or physiologically acceptable and/or pharmaceutically-acceptable carrier to enable CATA to be delivered to the desired target at an appropriate concentration. The carrier can itself be inert or it can possess cosmetic, physiological or pharmaceutical benefits of its own. The nature of the carrier will be dictated by the method chosen for administration of the composition. The method of administration of CATA composition may range from internal methods such as injection to external topical methods.

A preferred method of administration of CATA is by cutaneous injection. The carrier for facilitation of such administration would preferably comprise water or a saline solution, preferably an isotonic saline solution.

A more preferred method of administration of CATA is by topical application. Topical application is preferably achieved with compositions in the forms of lotions, solutions, ointments, sprays, tonics, creams, bars, shampoos, cream rinses, gels, sticks, mousse, pastes and the like.

Topical compositions of the present invention can be formulated as liquids, for example as a lotion, cream, shampoo, conditioner, gel, mousse or milk. Such liquid compositions may be formulated for use in conjunction with an applicator such as a roll-ball applicator, a tined applicator, a pad applicator, or a spray device such as an aerosol can containing propellant, or a container fitted with a pump to dispense the liquid product.

Alternatively, the compositions of the invention can be solid or semi-solid, for example sticks, creams or gels. Such solid or semi-solid compositions may be formulated for use in conjunction with a suitable applicator or simply a tube, or bottle, or as a liquid-impregnated fabric, such as a tissue wipe.

The selection of a carrier for this purpose presents a wide range of possibilities depending on the required product form of the composition. Suitable vehicles can be classified as described hereinafter.

The term "topical carrier" refers to substances which can act as diluents, dispersants, or solvents for CATA which therefore ensure that it can be applied to and distributed evenly over the selected target at an appropriate concentration. The carrier is preferably one which can aid penetration of CATA into the skin to reach the immediate environment of the hair follicle and/or sebaceous glands. Topical carriers useful in compositions of the subject invention can include water as a vehicle, and/or at least one cosmetically-acceptable vehicle other than water. Carriers useful in topical compositions according to the invention may include liposomes, latex latices, microspheres, cyclodextrans and various forms of microencapsulation of CATA.

Generally, the carrier is either organic in nature or an aqueous emulsion and capable of having CATA dispersed or dissolved therein. The carrier may include pharmaceutically-acceptable emollients, skin penetration enhancers, coloring agents, fragrances, emulsifiers, thickening agents, and solvents.

Topical compositions of the present invention may be formulated as a composition comprising an emollient. Such compositions typically comprise from about 1% to about 50%, preferably from about 5% to about 20% of a topical pharmaceutically-acceptable emollient; and a safe and effective amount of CATA.

As used herein, "emollients" refer to materials used for the prevention or relief of dryness, as well as for the protection of the skin. A wide variety of suitable emollients are known and may be used herein. Such emollients include, but are not limited to, hydrocarbon oils and waxes, silicon oils, triglyceride fats and oils, acetoglyceride esters, ethoxylated glycerides alkyl esters of fatty acids having 10 to 20 carbon atoms, alkenyl esters of fatty acids having 10 to 20 carbon atoms, fatty acids having 8–22 carbon atoms, fatty alcohols having 8–22 carbon atoms, fatty alcohol ethers, ether-esters, lanolin and derivatives, polyhydric alcohols and polyether derivatives, polyhydric alcohol ethers, wax esters, beeswax derivatives, vegetable waxes, phospholipids, sterols, and amides. SAGARIN, COSMETICS, SCIENCE AND TECHNOLOGY, 2nd Edition, Vol. 1, pp. 32–43 (1972), incorporated herein by reference, contains numerous examples of suitable materials.

Preferably the lotions of the present invention comprise a safe and effective amount of CATA; and from 1% to 50%, preferably from 3% to 15%, of an emollient.

Preferably the creams of the present invention comprise a safe and effective amount of CATA; from 5% to 50%, preferably from 10% to 25%, of an emollient; and the balance being water. The emollients described above can also be used in the cream compositions. Optionally the cream form contains a suitable emulsifier.

When an emulsifier is included, it is in the composition at a level from 3% to 50%, preferably from 5% to 20%.

Preferably the solution form of the present invention comprises a safe and effective amount of CATA, the balance being water and/or a suitable organic solvent. Suitable organic materials useful as the solvent or a part of a solvent system are as follows: dimethyl isosorbide, N-octyl pyrrolidone, propylene glycol, glycerine, polyethylene glycol (M.W. 200–600), polypropylene glycol (M.W. 425–2025), glycerine, sorbitol esters, 1,2,6-hexanetriol, ethanol, isopropanol, diethyl tartrate, butanediol and mixtures thereof Such solvent systems can also contain water.

Gel compositions of the present invention can be formulated by simply admixing a suitable thickening agent to the previously described solution compositions. The gel compositions preferably comprise a safe and effective amount of CATA; from 5% to 75%, preferably from 10% to 50%, of an organic solvent as previously described; and from 0.5% to 20%, preferably from 1% to 10% of the thickening agent.

Compositions of solid forms of the present invention have use as stick-type compositions intended for application to the scalp or other parts of the body. Such compositions preferably comprise a safe and effective amount of CATA, and from 50% to 98%, preferably from 60% to 90%, of the previously described emollients. This composition can further comprise from 1% to 20%, preferably from 5% to 15%, of a suitable thickening agent, and optionally emulsifiers and water. Thickening agents previously described with respect to lotions are suitable herein.

Skin cleaning compositions (preferably for use in the acne treatment and/or sebaceous gland activity treatment embodiment of the present invention) and scalp cleaning compositions (useful in both the acne and/or sebaceous gland treatment, and hair growth regulation embodiments of the present invention), comprise, in addition to CATA, a cosmetically-acceptable surfactant.

The cleaning compositions useful in the subject invention preferably contain a safe and effective amount of CATA and preferably from about 1% to about 90%, more preferably from about 5% to about 10%, of a cosmetically-acceptable surfactant.

The physical form of the cleansing compositions is not critical. The compositions can be, for example, formulated as toilet bars, liquids, shampoos, pastes, or mousses. Toilet bars are most preferred since this is the form of cleansing agent most commonly used to wash the skin. Rinse-off cleansing compositions, such as shampoos, require a delivery system adequate to deposit sufficient levels of CATA on the skin and scalp. A preferred delivery system involves the use of insoluble complexes. For a more complete disclosure, see U.S. Pat. No. 4,835,148, Barford et al., issued May 30, 1989; incorporated herein by reference in its entirety.

The surfactant component of the compositions useful in the subject invention are selected from anionic, nonionic, zwitterionic, amphoteric and ampholytic surfactants, as well as mixtures of these surfactants. Such surfactants are well-known to those skilled in the detergency art.

The cleaning compositions useful in the subject invention can optionally contain, at their an-established levels, materials which are conventionally used in cleansing compositions. Nonlimiting examples of possible surfactants include isoceteth-20, sodium methyl cocoyl taurate, sodium methyl oleoyl taurate, and sodium lauryl sulfate. See U.S. Pat. No. 4,800,197, to Kowcz et al., issued Jan. 24, 1989, which is incorporated herein by reference in its entirety. Examples of a broad variety of additional surfactants useful herein are described in McCutcheon's, DETERGENTS AND EMULSIFIERS, North American Edition (1986), published by Allured Publishing Corporation, which is incorporated herein by reference in its entirety.

Acne-Combination Actives

The compositions of the present invention useful for treating acne or sebaceous gland activity can also comprise, in addition to CATA, actives such as anti-inflammatory agents, retinoids, antimicrobial agents, antiandrogens, and/or comedolytic agents, for the treatment of acne and/or sebaceous gland activity.

A. Anti-inflammatory agents

An anti-inflammatory agent may be included as an active along with CATA, for treatment of acne and/or sebaceous gland activity. A safe and effective amount of an anti-inflammatory agent may be added to the compositions useful in the subject invention, preferably from about 0.1% to about 10%, more preferably from about 0.5% to about 5%, of the composition. The exact amount of anti-inflammtory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone.

A second class of anti-inflammatory agents which is useful in the compositions includes the non-steroidal anti-inflammatory agents. The variety of compounds encompassed by this group are well-known to those skilled in the art. For detailed disclosure of the chemical structure, synthesis, side effects, etc. of non-steroidal anti-inflammatory agents, reference may be had to standard texts, including ANTI-INFLAMMATORY AND ANTI-RHEUMATIC DRUGS, K. D. Rainsford, Vol. I–III, CRC Press, Boca Raton, (1985), and ANTI-INFLAMMATORY AGENTS, CHEMISTRY AND PHARMACOLOGY, 1, R. A. Scherrer, et al., Academic Press, New York (1974), both of which are incorporated herein by reference.

Specific non-steroidal anti-inflammatory agents useful in compositions of the present invention include, but are not limited to:

1) the oxicams, such as piroxicam, isoxicam, tenoxicam, sudoxicam, and CP-14,304;

2) the salicylates, such as aspirin, disalcid, benorylate, trilisate, safapryn, solprin, diflunisal, and fendosal;

3) the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac;

4) the fenamates, such as mefenamic, meclofenamic, fluofenamic, niflumic, and tolfenamic acids;

5) the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and 6) the pyrazoles, such as phenylbutazone, oxyphenbutazone, feprazone, azapropazone, and trimethazone.

Mixtures of these non-steroidal anti-inflammatory agents may also be employed, as well as the pharmaceutically-acceptable salts and esters of these agents. For example, etofenamate, a flufenamic acid derivative, is particularly useful for topical application. Of the non-steroidal anti-inflammatory agents, ibuprofen, naproxen, flufenamic acid, mefenamic acid, meclofenamic acid, piroxicam and felbinac are preferred; ibuprofen, naproxen, and flufenamic acid are most preferred.

Finally, so-called "natural" anti-inflammatory agents are useful in methods of the subject invention. For example, candelilla wax, alpha bisabolol, aloe vera, Manjistha (extracted from plants in the genus Rubia, particularly *Rubia Cordifolia*), and Guggal (extracted from plants in the genus Commiphora, particularly *Commiphora Mukul*), may be used.

B. Retinoids

In a preferred acne and/or sebaceous gland treating composition useful in the subject invention, a retinoid, preferably retinoic acid, is included as an active along with CATA. The inclusion of a retinoid increases the acne and/or sebaceous gland treating benefits of the composition. A safe and effective amount of a retinoid may be added to the compositions useful in the subject invention, preferably from about 0.001% to about 0.5%, more preferably from about 0.01% to about 0.1% of the composition. As used herein, "retinoid" includes all natural and/or synthetic analogs of Vitamin A or retinol-like compounds which possess the biological activity of Vitamin A in the skin as well as the geometric isomers and stereoisomers of these compounds, such as all-trans retinoic acid and 13-cis-retinoic acid.

C. Antimicrobial agents

In a preferred acne and/or sebaceous gland treating composition useful in the subject invention, an antimicrobial agent is included as an active along with CATA. The inclusion of an antimicrobial agent increases the acne-treating benefits of the composition. As used herein, "antimicrobial agent" means a compound capable of destroying microbes, preventing the development of microbes or preventing the pathogenic action of microbes.

A safe and effective amount of an antimicrobial agent may be added to compositions useful in the subject invention, preferably from about 0.001% to about 5%, more preferably from about 0.01% to about 2%, more preferably still from about 0.05% to about 1% of the compositions. Preferred antimicrobial agents useful in the subject invention are benzoyl peroxide, erythromycin, tetracycline, clindamycin, azelaic acid, and sulfur resorcinol.

D. Comedolytic agents

In a preferred ache and/or sebaceous gland treating composition useful in the subject invention, a comedolytic agent is included as an active along with CATA.

As used herein, the term "comedolytic agent" refers to any compound capable of rupturing a comedo.

A safe and effective amount of a comedolytic agent may be added to the compositions useful in the subject invention, preferably from about 0.05% to about 10%, more preferably from about 0.1% about 5%.

A preferred comedolytic agent useful in the subject invention is salicylic acid.

Hair Growth—Combination Actives

The compositions of the present invention useful for regulating hair growth can also optionally comprise other hair growth stimulants capable of functioning in different ways to enhance the benefit of CATA. An example of such a substance includes, but is not limited to minoxidil, and derivatives thereof, as disclosed in U.S. Pat. Nos., 3,461,461; 3,973,061; 3,464,987; and 4,139,619; incorporated herein by reference.

Additional hair growth stimulants useful in compositions of the present invention comprising CATA include the agents disclosed by the following, which are all incorporated herein by reference: U.S. Pat. No. 5,215,760, Kauvossi and Kauvossi, issued Jun. 1, 1993; U.S. Pat. No. 5,192,534, Grollier and Richoux, issued Mar. 9, 1993; U.S. Pat. No. 5,178,883, Knighton, issued Jan. 12, 1993; U.S. Pat. No. 5,177,061, Pickart, issued Jan. 5, 1993; U.S. Pat. No. 5,130,142, Wong and Warren, issued Jul. 14, 1992; U.S. Pat. No. 5,068,315, Buultjens, Colin, Jahoda and Oliver, issued Nov. 26, 1991; U.S. Pat. No. 5,091,173, Buultjens, Hellens, Oliver and Withers, issued Feb. 25, 1992; U.S. Pat. No. 5,037,643, Green, issued Aug. 6, 1991; U.S. Pat. No. 4,975,441, Gibson, issued Dec. 4, 1990; U.S. Pat. No. 4,871,839, Gibson, issued Oct. 3, 1989; U.S. Pat. No. 4,832,946, Green, issued May 23, 1989; U.S. Pat. No. 4,761,401, Couchman, issued Aug. 2, 1988; U.S. Pat. No. 4,139,619, Chidsey, issued Feb. 13, 1979; U.S. Pat. No. 3,466,364, Takahashi, issued Sep. 9, 1969; and U.S. Pat. No. 1,732,120, Christen, issued Oct. 15, 1929; and PROSCAR® (a.k.a., finasteride or (5α, 17β)-1-1-Dimethylethyl)-3-oxo-4-azaandrost-1-ene-17-carboxamide; Merck & Co.) see THE MERCK INDEX, 11th Ed., p. 1250, entry 7888.

Delivery Methods for Topical Compositions

The topical compositions useful for the methods of the instant invention can be delivered from a variety of delivery devices. The following are two nonlimiting examples.

A. Medicated cleansing pads

The compositions useful herein can be incorporated into a medicated cleansing pad. Preferably these pads comprise from about 50% to about 75% by weight of one or more layers of nonwoven fabric material and from about 20% to about 50% by weight of a liquid composition deliverable from the nonwoven fabric material preferably comprising from about 0.01% to about 10% CATA, more preferably from about 0.5% to about 2%, more preferably still from about 0.1% to about 1%. These pads are described in detail in U.S. Pat. No. 4,891,228, to Thaman et al., issued Jan. 2, 1990; and U.S. Pat. No. 4,891,227, to Thaman et al., issued Jan. 2, 1990; both of which are incorporated by reference.

B. Dispensing devices

The compositions useful herein can also be incorporated into and delivered from a soft-tipped or flexible dispensing device. These devices are useful for the controlled delivery of the compositions to the skin surface and have the advantage that the treatment composition itself never need be directly handled by the user. Nonlimiting examples of these devices comprise a fluid container including a mouth, an applicator, means for holding the applicator in the mouth of the container, and a normally closed pressure-responsive valve for permitting the flow of fluid from the container to the applicator upon the application of pressure to the valve. The fluid preferably contains from about 0.05% to about 15% CATA, more preferably from about 0.5% to about 3%, more preferably still from about 0.1% to about 1%.

The valve can include a diaphragm formed from an elastically fluid impermeable material with a plurality of non-intersecting arcuate slits therein, where each slit has a base which is intersected by at least one other slit, and where each slit is out of intersecting relation with its own base, and wherein there is a means for disposing the valve in the container inside of the applicator. Examples of these applicator devices are described in U.S. Pat. No. 4,693,623, to Schwartzman, issued Sep. 15, 1987; U.S. Pat. No. 4,620,648, to Schwartzman, issued Sep. 15, 1987; U.S. Pat. No. 3,669,323, to Harker et al., issued Jun. 13, 1972; U.S. Pat. No. 3,418,055, to Schwartzman, issued Dec. 24, 1968; and U.S. Pat. No. 3,410,645, to Schwartzman, issued Nov. 12, 1968; all of which are incorporated herein by reference. Examples of applicators useful herein are commercially available from Dab-O-Matic, Mount Vernon, N.Y.

Methods for Treating Acne and/or Sebum Activity

One embodiment of the present invention relates to methods for treating acne and controlling sebum in mammalian skin and scalp. Such methods may comprise topically applying to the skin an effective amount of the compositions of the subject invention. The term "effective amount", as used herein with regard to acne or sebum activity treatment, means an amount sufficient to provide an anti-acne or sebum-control benefit. The composition can be applied for several days, weeks, months, or years at appropriate intervals: from about four times a day to about once every three days, preferably from about three times a day to about once every other day, more preferably about twice to once a day until existent acne subsides; and preferably from about twice a day to about once every other day, more preferably about once a day to prevent or retard the onset of acne. The composition is preferably applied from about twice a day to about once every three days, more preferably about once every other day to control oily skin and scalp.

Typically, in each application, an effective coating of the skin or scalp is achieved by applying from about 0.01 to about 1,000 $\mu g/cm^2$ skin or scalp per application of the active CATA; preferably from about 0.1 to about 500 $\mu g/cm^2$ skin or scalp per application; more preferably from about 1 to about 200 μg/cm² skin or scalp per application; more preferably from about 10 to about 100 μg/cm² skin or scalp per application.

Methods for Regulating Hair Growth

An alternative embodiment of the present invention provides for the use of CATA for regulating hair growth in mammals (e.g., humans and domestic animals). In one embodiment, the present invention provides for the use of CATA for preventing hair loss. Such prophylactic application is particularly useful to individuals who have a family history of baldness. In another embodiment, the present invention provides for the use of CATA for stimulating new hair growth. Preferably, CATA is applied to mammals in need of hair growth regulation, more preferably to mammals suffering from hair loss. The following methods of use may be used to regulate hair growth.

The compositions according to the invention are preferably intended for application by cutaneous injection. The amount of the composition and the frequency of cutaneous injection can vary widely, depending on personal needs. As an example of application by cutaneous injection, it is suggested that a composition suitable for cutaneous injection comprising CATA be cutaneously injected preferably from about once per day to about once every six months, more preferably from about once per week to about twice per month. The composition for cutaneous injection will preferably administer from about 0.01 to about 1 mg of CATA per cm² skin receiving cutaneous injection, more preferably from about 0.02 to about 0.5 mg/cm², more preferably still from about 0.05 to about 0.1 mg/cm². The period of injections would be over a period of from about one month to the life of the subject, more preferably, in the case of humans, from about 1 month to about ten years, more preferably from about three months to about two years, more preferably still from about six months to about one year, thereby resulting in regulation of hair growth.

A more preferred method of applying the compositions according to the present invention involves topical application to the scalp of a human subject or the skin of a domesticated animal subject to regulate hair growth, particularly where the scalp/skin is already bald or balding. The amount of the composition and the frequency of application to the hair and/or scalp/skin can vary widely, depending on the desired effect and/or personal needs, but it is suggested as an example that topical application preferably range from about 1 to about 10 times daily, more preferably from about 3 to about 6 times daily, more preferably still from about 2 to about 3 times daily, and most preferably about once per day.

The composition for topical application will preferably contain from about 0.01 to about 1,000 μg of CATA per cm² skin receiving the topical composition, more preferably from about 0.1 to about 500 μg/cm², more preferably still from about 1 to about 200 μg/cm², more preferably from about 10 to about 100 μg/cm². The period of topical application may be over the subject's life, but would preferably, in the case of a human subject, be over a period of from about one month to about ten years, more preferably from about three months to about two years, more preferably still from about six months to about one year, thereby resulting in regulation of hair growth.

In another embodiment of the present invention, hair growth regulation is achieved by topical administration of a composition of the present invention and oral administration of an antiandrogen (e.g., finasteride, cyproterone acetate) during the same treatment period.

EXAMPLES

The composition embodiments of the present invention are illustrated in the following examples. All pans, percentages, and ratios used herein are by weight unless otherwise specified.

A. Acne

Examples 1–3

Topical compositions are prepared by combining the following components utilizing conventional mixing techniques:

| Component | Example No. | | |
|---|---|---|---|
| | 1 | 2 | 3 |
| Cyproterone acetate thioacetate | 0.1 | 1.0 | 10.0 |
| N-octyl pyrrolidone | 1.0 | 3.0 | 5.0 |
| Glycerol | 1.0 | 2.0 | 3.0 |
| Perfume | 0.2 | 0.2 | 0.2 |
| Dimethyl isosorbide | balance to 100% | | |

Any of the above compositions is applied to the face, to treat oily skin, at a dose of 0.1 ml, four times a day. As the skin becomes less oily, application is reduced to twice daily.

Examples 4–6

Oil-in-water lotions are prepared, containing the following compositions, using conventional mixing techniques:

| Component | Example No. | | |
|---|---|---|---|
| | 4 | 5 | 6 |
| Oily Phase | | | |
| Cyproterone acetate thioacetate | 0.5 | 2.0 | 5.0 |
| Cetearyl alcohol | 1.0 | 2.0 | 5.0 |
| Silicon oil, 200 fluid | 1.0 | 1.0 | 1.0 |
| Isopropyl myristate | 2.0 | 2.0 | 2.0 |
| Sodium stearoyl-2-lactylate | 2.0 | 2.0 | 2.0 |
| Aqueous Phase | | | |
| Propylene glycol | 5.0 | 5.0 | 5.0 |
| Sodium citrate | 0.2 | 0.2 | 0.2 |
| Perfume | 0.1 | 0.1 | 0.1 |
| Water | balance to 100% | | |

The emulsion is prepared by taking 10 parts of the oily phase and adding to it slowly with stirring 90 parts by volume of the aqueous phase. Use of an amount of the emulsion to deposit about 0.05 mg/cm² of CATA to the skin is appropriate to treat existing acne. Application of the emulsion about twice a day is appropriate.

Examples 7–8

Oil-in-water creams are prepared by mixing the following components:

| Component | Example No. | |
|---|---|---|
| | 7 | 8 |
| Oily Phase | | |
| Cyproterone acetate thioacetate | 1.0 | 2.0 |
| Sorbitan monoleate | 10.0 | 20.0 |
| Quaternium-18-hectonite | 3.0 | 5.0 |

|                        | Example No. | |
|------------------------|------|------|
| Component              | 7    | 8    |
| Liquid paraffin        | 30.0 | 60.0 |
| Aqueous Phase          |      |      |
| Xanthan gum            | 1.0  | 1.0  |
| Preservative           | 0.3  | 0.3  |
| Perfume                | 0.2  | 0.2  |
| Water                  | balance to 100% | |

The cream is prepared by mixing the oily phase and heating to 65° C. The aqueous phase is combined and heated to 70° C. The aqueous phase is added to the oil phase with suitable agitation. Moderate agitation is applied while cooling. Topical application of the cream is suitable to treat acne or control sebum. Use of an amount of the composition to deposit about 0.04 mg/cm$^2$ of CATA to the skin is appropriate to treat oily skin. Application occurs about once a day. When the skin becomes less oily, application is reduced to once every other day.

Examples 9-11

The following lotions are prepared by mixing the ingredients in each composition according to conventional mixing techniques:

|                              | Example No. | | |
|------------------------------|------|------|------|
| Component                    | 9    | 10   | 11   |
| Cyproterone acetate thioacetate | 0.1  | 2.0  | 10.0 |
| Benzoyl peroxide             | 2.0  | 5.0  | 10.0 |
| N-octyl pyrrolidone          | 1.0  | 3.0  | 5.0  |
| Perfume                      | 0.2  | 0.2  | 0.2  |
| Dimethyl isosorbide          | balance to 100% | | |

Any of the above compositions is applied to the face at a dose of 0.2 ml, four times a day to treat existing acne. As the ache subsides, application is reduced to once a day.

Examples 12-14

The following lotions are prepared by mixing the ingredients in each composition according to conventional mixing techniques:

|                              | Example No. | | |
|------------------------------|------|------|------|
| Component                    | 12   | 13   | 14   |
| Cyproterone acetate thioacetate | 0.01 | 0.1  | 5.0  |
| Salicylic acid               | 0.5  | 2.0  | 5.0  |
| N-octyl pyrrolidone          | 1.0  | 3.0  | 5.0  |
| Perfume                      | 0.2  | 0.2  | 0.2  |
| Dimethyl isosorbide          | balance to 100% | | |

Use of an amount of any of the above compositions to deposit about 0.01 mg/cm$^2$ of CATA to the skin is appropriate to treat existing ache. Application occurs once a day.

Examples 5-17

The following lotions are prepared by mixing the ingredients in each composition according to conventional mixing techniques:

|                              | Example No. | | |
|------------------------------|------|------|------|
| Component                    | 15   | 16   | 17   |
| Cyproterone acetate thioacetate | 0.3  | 1.0  | 3.0  |
| Erythromycin                 | 0.5  | 2.0  | 4.0  |
| N-octyl pyrrolidone          | 1.0  | 3.0  | 5.0  |
| Perfume                      | 0.2  | 0.2  | 0.2  |
| Dimethyl isosorbide          | balance to 100% | | |

Use of an amount of any of the above lotions to deposit about 0.1 mg/cm$^2$ of CATA to the scalp is appropriate to treat excess oil in the scalp. Application occurs once every two days.

Examples 18-20

The following lotions are prepared by mixing the ingredients in each composition according to conventional mixing techniques:

|                              | Example No. | | |
|------------------------------|------|------|------|
| Component                    | 18   | 19   | 20   |
| Cyproterone acetate thioacetate | 0.1  | 2.0  | 10.0 |
| Azeleic acid                 | 1.0  | 5.0  | 20.0 |
| N-octyl pyrrolidone          | 1.0  | 3.0  | 5.0  |
| Perfume                      | 0.2  | 0.2  | 0.2  |
| Dimethyl isosorbide          | balance to 100% | | |

Any of the above compositions is applied to the face at a dose of 0.2 ml, three times a day to treat oily skin. As the skin becomes less oily, application is reduced to once a day.

Example 21

The following shampoo is prepared by mixing the ingredients according to conventional mixing techniques:

| Component                         | Example No. 21 |
|-----------------------------------|------|
| Cyproterone acetate thioacetate   | 2.0  |
| Triethanolamine lauryl sulfate    | 17.0 |
| Coconut diethanolamide            | 2.0  |
| Hydroxypropylmethyl cellulose*    | 0.2  |
| Corn syrup (80% solids)**         | 30.0 |
| Dimethylpolysiloxane              | 1.0  |
| Catiionic cellulose***            | 0.5  |
| Ethyl alcohol (SDA 40)            | 9.0  |
| Vinyl carboxy polymer****         | 0.7  |
| Perfume, color, preservative      | 1.0  |
| Water                             | balance to 100% |
| Acid or base to pH 6.5            |      |

*Methocel E4M (Dow Chemical)
**42 Dextrose equivalent (Staley 1300)
***Polymer JR 400
****Carbopol 941 (BF Goodrich)

The composition is applied to the scalp every other day to treat excess oil in the scalp. A dose of about 0.5 ml is applied and washed off.

Example 22

The following lotion/hair tonic is prepared by mixing the ingredients according to conventional mixing techniques.

| Component                         | Example No. 22 |
|-----------------------------------|------|
| Cyproterone acetate thioacetate   | 10.0 |
| Pyroglutamic acid methyl ester    | 10.0 |

-continued

| Component | Example No. 22 |
|---|---|
| N-octyl pyrrolidone | 5.0 |
| Perfume | 0.3 |
| Dimethyl isosorbide | balance to 100% |

The composition is applied every three days at a dose of about 0.4 ml to treat excess oil in the scalp. The tonic is left on after application.

B. Hair growth

Example 23

An injectable composition is prepared by combining the following components utilizing conventional mixing techniques.

| Component | Example No. 23 |
|---|---|
| Cyproterone acetate thioacetate | 0.05 |
| Saline | balance to 100% |

0.1 cc of the composition per $cm^2$ skin is injected at the site of desired hair regulation once every two weeks for six months to a subject resulting in new hair growth.

Examples 24–26

The following topical solutions are prepared by combining the following components utilizing conventional mixing techniques.

| Component | Example No. | | |
|---|---|---|---|
| | 24 | 25 | 26 |
| Cyproterone acetate thioacetate | 0.01 | 1.00 | 5.00 |
| N-octyl pyrrolidone | 1.00 | 3.00 | 5.00 |
| Perfume | 1.00 | 1.00 | 1.00 |
| Dimethyl isosorbide | balance to 100% | | |

1000 mg of the composition per 100 $cm^2$ skin is topically applied twice per day for one year to a subject resulting in new hair growth.

Examples 27–29

The following conditioning lotions are prepared by combining the following components utilizing conventional mixing techniques.

| Component | Example No. | | |
|---|---|---|---|
| | 27 | 28 | 29 |
| Cyproterone acetate thioacetate | 0.01 | 1.00 | 5.00 |
| Ammonium laureth sulfate | 6.00 | 6.00 | 6.00 |
| Disodium cocoamphodiacetate | 3.00 | 3.00 | 3.00 |
| Alkyl polyglucosides | 2.70 | 2.70 | 2.70 |
| Glycerine | 5.00 | 5.00 | 5.00 |
| Dimethicone copolyol | 2.00 | 2.00 | 2.00 |
| Polyol alkoxy ester | 1.20 | 1.20 | 1.20 |
| Polyquat 10 | 1.00 | 1.00 | 1.00 |
| Sodium benzoate | 0.25 | 0.25 | 0.25 |
| DMDM hydantoin* | 0.14 | 0.14 | 0.14 |
| Disodium EDTA** | 0.13 | 0.13 | 0.13 |
| Mineral oil | 4.00 | 4.00 | 4.00 |
| Myristic acid | 1.10 | 1.10 | 1.10 |
| Polyethylene glycol caprylic/capric glycerides | 2.00 | 2.00 | 2.00 |
| Titanium doxide | 0.10 | 0.10 | 0.10 |
| Perfume | 1.00 | 1.00 | 1.00 |
| Water | balance to 100% | | |

*1,3-dihydroxymethyl-3,3-dimethyl hydantoin
**ethylenediaminetetraacetic acid 1000 mg of the composition per 100 $cm^2$ skin is topically applied once per day for 6 months to a subject resulting in prevention of hair loss.

Examples 30–32

The following shampoo compositions are prepared by combining the following components utilizing conventional mixing techniques.

| Component | Example No. | | |
|---|---|---|---|
| | 30 | 31 | 32 |
| Cyproterone acetate thioacetate | 0.01 | 1.00 | 5.00 |
| Ammonium laureth sulfate | 6.00 | 6.00 | 6.00 |
| Disodium cocoamphodiacetate | 3.00 | 3.00 | 3.00 |
| Alkyl polyglucosides | 2.70 | 2.70 | 2.70 |
| Glycerine | 5.00 | 5.00 | 5.00 |
| Dimethicone copolyol | 2.00 | 2.00 | 2.00 |
| Polyol alkoxy ester | 1.20 | 1.20 | 1.20 |
| Polyquat 10 | 1.00 | 1.00 | 1.00 |
| Sodium benzoate | 0.25 | 0.25 | 0.25 |
| DMDM hydantoin* | 0.14 | 0.14 | 0.14 |
| Disodium EDTA** | 0.13 | 0.13 | 0.13 |
| Titanium dioxide | 0.10 | 0.10 | 0.10 |
| Perfume | 1.00 | 1.00 | 1.00 |
| Water | balance to 100% | | |

*1,3-dihydroxymethyl-3,3-dimethyl hydantoin
**ethylenediaminetetraacetic acid

This composition may be used in a conventional manner for cleaning hair, while bestowing hair growth regulation to the subject. From about 0.1 g to about 10g of the composition is applied to hair that has been wetted, generally with water, worked through the hair and then rinsed out.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of the invention.

What is claimed is:

1. A compound having the structure

[chemical structure diagram]

2. A pad for topical delivery of an active comprising:
   a. from about 50% to about 75% by weight of one or more layers of nonwoven fabric material; and
   b. from about 25% to about 50% by weight of a liquid composition, deliverable from the nonwoven fabric material, comprising from about 0.01% to about 10% of a compound having the structure:

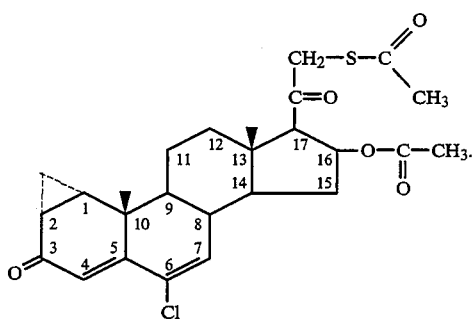

3. A fluid dispensing device comprising:
a. a fluid container with a mouth;
b. a soft, porous-tipped applicator at an end of the fluid container;
c. a means for holding the applicator in the mouth of the container; and
d. a liquid composition, deliverable from the fluid container through the applicator onto the skin, comprising from about 0.01% to about 10% of a compound having the structure

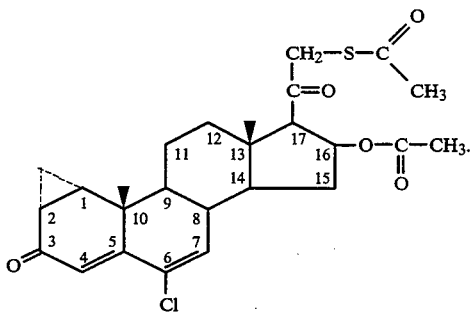

4. A composition comprising:
a. a safe and effective amount of a compound having the structure

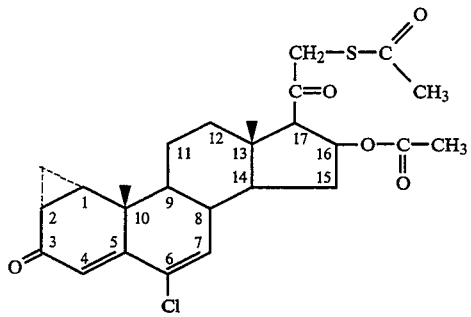

b. a pharmaceutically-acceptable or cosmetically-acceptable carrier.

5. The composition of claim 4, wherein the carrier is a topical carrier.

6. The composition of claim 5, wherein the composition comprises from about 0.001% to about 5% of the compound.

7. The composition of claim 4, wherein the carrier is an injectable carrier.

8. The composition of any one of claims 4, 5 or 6, wherein the composition additionally comprises an acne treating agent selected from the group consisting of anti-inflammatory agent, retinoid, antimicrobial agent, antiandrogen and comedolytic agent.

9. A method of treating acne comprising topical application of the composition of any one of claims 4, 5 or 6.

10. A method of treating excessive sebaceous gland activity in mammalian skin and scalp comprising topical application of the composition of any one of claims 4, 5 or 6.

11. A method of regulating hair growth comprising administration of the composition of any one of claims 4, 5, 6 or 7.

* * * * *

UNITED STATES PATENT AND TRADEMARK OFFICE
CERTIFICATE OF CORRECTION

PATENT NO. : 5,344,651

DATED : September 6, 1994

INVENTOR(S) : Richard J. Schwen et al.

It is certified that error appears in the above-identified patent and that said Letters Patent is hereby corrected as shown below:

Column 18, line 29, "ache" should read --acne--.

Signed and Sealed this

Thirtieth Day of May, 1995

Attest:

BRUCE LEHMAN

*Attesting Officer*        *Commissioner of Patents and Trademarks*